Figure 1:
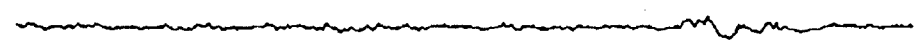
Figure 1:
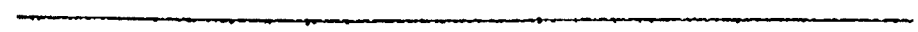
Figure 1:
Figure 1:
Figure 1:
Figure 1:
Figure 1:
Figure 1:
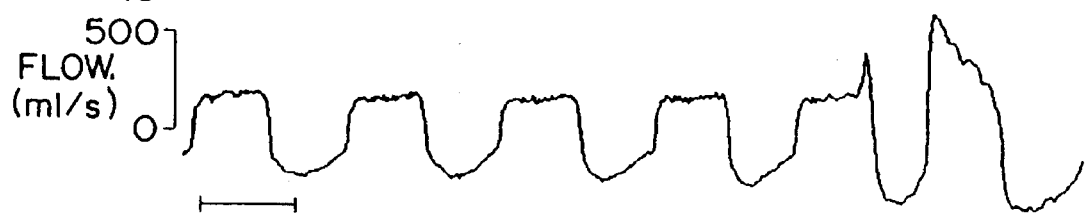
Figure 1:
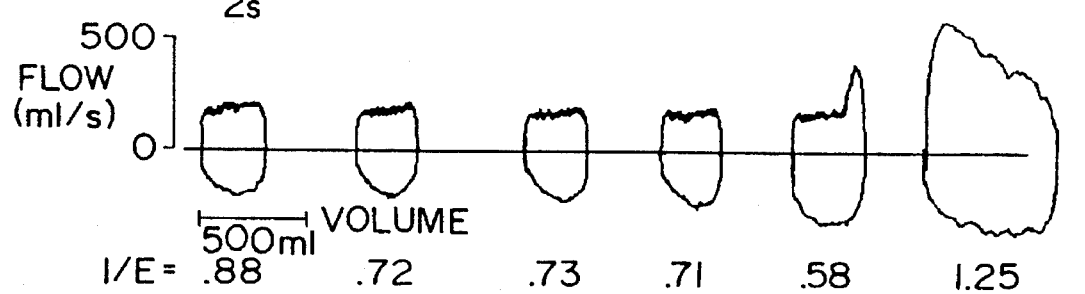

United States Patent [19]

Series et al.

[11] Patent Number: 5,456,264
[45] Date of Patent: Oct. 10, 1995

[54] ACCURACY OF BREATH-BY-BREATH ANALYSIS OF FLOW VOLUME LOOP IN IDENTIFYING FLOW-LIMITED BREATHING CYCLES IN PATIENTS

[75] Inventors: Frédérick Series; Isabelle Marc, both of Ste-Foy, Canada

[73] Assignee: Universite Laval, Quebec, Canada

[21] Appl. No.: 220,733

[22] Filed: Mar. 31, 1994

[51] Int. Cl.$^6$ ..................................................... A61B 5/08
[52] U.S. Cl. ........................................ 128/725; 128/720
[58] Field of Search ................................. 128/716, 720, 128/725, 204.18, 204.21, 204.23, 204.26, 207.18

[56] References Cited

U.S. PATENT DOCUMENTS

| | | | |
|---|---|---|---|
| 4,957,107 | 9/1990 | Sipin | 128/204.18 |
| 5,107,831 | 4/1992 | Halpern et al. | 128/204.26 |
| 5,199,424 | 4/1993 | Sullivan et al. | 128/716 |
| 5,335,654 | 8/1994 | Rapoport | 128/204.21 |

OTHER PUBLICATIONS

Anch A M, et al. (1982). *J Appl Physiol.* 53(5): 1158–1163.
Baydur A, et al. (1982). *Am Rev Repir Dis.* 126: 788–791.
Bradley T D, et al. (1986). *N Engl J Med.* 315(21): 1327–1331.
Condos, R, et al. (1993). *Am Rev Respir Dis.* 147: A251.
Gleadhill, I C, et al. (1991). *Am Rev Respir Dis.* 143: 1300–1303.
Gould G A, et al. (1988). *Am Rev Respir Dis.* 137: 895–898.
Guilleminault C, et al. (1993). *Chest.* 104: 781–787.
Haponik E F, et al. (1983). *Am Rev Respir Dis.* 127: 221–226.
Haponik E F, et al. (1981). *Am Rev Respir Dis.* 124: 571–574.
Hoffstein V, et al. (1989). *Am Rev Respir Dis.* 139: 957–960.
Hudgel D W, et al. (1988). *J Appl Physiol.* 64 (5): 1930–1935.
Isono S, et al. (1993). *J Appl Physiol.* 75 (1): 148–154.
Kayaleh R F, et al. (1992). *Am Rev Respir Dis.* 145: 1372–1377.
Krieger J, et al. (1985). *Chest* 87: 163–167.
Mahadevia A K, et al. (1983). *Am Rev Respir Dis.* 128: 708–711.
Martin R J., chairman (1989) *Am Rev Respir Dis.* 139: 559–568.
Rodenstein D O, et al. (1984). *J Appl Physiol.* 57 (3): 651–657.

(List continued on next page.)

*Primary Examiner*—Lee S. Cohen
*Assistant Examiner*—Brian M. Green
*Attorney, Agent, or Firm*—Merchant, Gould, Smith, Edell, Welter & Schmidt

[57] ABSTRACT

Inspiratory flow limitation (IFL) is involved in the pathophysiology of sleep-related breathing disorders. Since the definition of flow-limited cycle is based on a dissociation between flow and respiratory efforts, identification of IFL requires upper airway or intrathoracic pressure measurements. We examined the feasibility and accuracy of the analysis of the flow-volume loop of a tidal breath in identifying IFL. The tidal volume was obtained by integration of the instantaneous airflow signal, and the flow-volume loop was reconstructed for each breathing cycle by plotting the instantaneous flow and the tidal volume. The instantaneous inspiratory and expiratory flows were measured at a 50% of the respective (inspiratory or expiratory) portion of the tidal volume, and a breath-by-breath analysis of the mid tidal volume flow ratio (I/E ratio) was obtained. There was a positive significant relationship between I/E ratio and $V_{Imax}$ (maximal inspiratory volume) for flow-limited breathing (correlation coefficient range: 0.25–0.54). With a lower limit of the normal I/E ratio threshold of 0.97, the sensitivity and specificity of the method were both 76%. Patients having a I/E ratio lower than 0.97 to 1 are classified as suffering IFL. Therefore, the prevent invention relates to the above-described non-invasive method which is applicable in the evaluation IFL and to an apparatus measuring I/E ratio and correcting IFL.

6 Claims, 3 Drawing Sheets

OTHER PUBLICATIONS

Sanders N H. and N. Kern (1990). *Chest.* 98: 317–324.
Sanders M H and S E Moore (1983). *Am Rev Respir Dis.* 127: 554–558.
Sanders M H, et al. (1981). *JAMA* 245 (23): 2414–2418.
Schwartz A R, et al. (1989). *J Appl Physiol.* 66 (4): 1626–1634.
Séri`es F, and I Marc (1993). *J Appl Physiol.* 75 (3): 1222–1225.
Séri`es F, et al. (1990). *J Appl Physiol.* 68 (5): 2159–2164.
Shepard J W, and C D Burger (1990). *Am Rev Respir Dis.* 142: 1288–1293.
Shore E T and R P Millman (1984). *Thorax.* 39: 775–779.
Smith P L, et al. (1988). *J Appl Physiol.* 64 (2): 789–795.
Suratt P M, et al. (1983). *Am Rev Respir Dis* 127: 487–492.
Tammelin B R, et al. (1983).*Am Rev Respir Dis.* 128: 712–715.

EOG

EMG

EEG
 $C_3$-$A_2$
 $C_4$-$A_1$
 $O_1$-$A_2$
 $O_2$-$A_1$

PES (cmH2O)

FLOW (ml/s)

2s

FLOW (ml/s)

500ml VOLUME

I/E = .88  .72  .73  .71  .58  1.25

ACCURACY OF BREATH-BY-BREATH ANALYSIS OF FLOW VOLUME LOOP IN IDENTIFYING FLOW-LIMITED BREATHING CYCLES IN PATIENTS

FIELD OF THE INVENTION

Sleep apnea hypopnea syndrome (SAHS) is characterized by recurrent episodes of upper airway (UA) closure. Anatomic abnormalities of UA that tend to decrease UA calibre are frequently but not always observed in SAHS. Even in the absence of such abnormalities, UA diameter is smaller in SAHS than in normals (1,2). These abnormalities may be involved in the increase in UA resistance observed in these patients when awake (3). The repercussions of UA abnormalities on airflow pattern have been studied during wakefulness and sleep. During wakefulness, abnormalities of the flow-volume loops are useful in documenting the presence of an extra thoracic obstruction. These abnormalities have been proposed to identify SAHS patients (4–6). However, they cannot be used as a reliable screening test because of their poor sensitivity, and the absence of difference between apneic and non-apneio snorers (7,8). These negative results can be explained by the techniques used to obtain these loops; the subjects are in the sitting position (9,10), and breath exclusively by the mouth (10) which is not the usual breathing route (11). Furthermore, the loops are effort-dependant and tidal breath flow-volume curves may differ between SAHS and non-apneic subjects when awake (12). During sleep, UA may behave like a Starling resistor (13) with the occurrence of flow-limited regimen (14). The flow pattern depends on the inspiratory transmural pharyngeal pressure gradient, the force generated by UA dilators, and the compliance of UA tissues. In SAHS, the increase in UA collapsibility leads to inspiratory flow limitation (IFL) (15, 16) that is responsible for partial or complete UA closure. Besides its involvement in the occurrence of obstructive apneic and hypopneic event, IFL can contribute to the pathophysiology of sleep-related breathing disorders by causing sleep fragmentation (17).

The diagnosis of SAKS is based in polysomnographic studies; changes in oro-nasal flow and in thoraco-abdominal movements are used to define sleep-related breathing disorders (18,19). These signals are qualitative or semi-quantitative and cannot identify IFL since it is characterized by a plateauing on the inspiratory flow with increasing respiratory efforts that requires the measurements of flow and supralaryngeal or intrathoracic pressure.

STATEMENT OF THE INVENTION

From previously described data, it appears that flow analysis may be of first importance in identifying nocturnal breathing abnormalities. Since IFL results from the dynamic narrowing of UA during inspiration, we hypothesised that it should be accompanied by significant changes in the flow-volume loop and that the breath-by-breath analysis of this loop could be used to determine the presence of IFL. If accurate, this analysis would represent a simple, quantitative, and non-invasive method for characterizing sleep-related breathing disorders. The present invention therefore relates to a method of evaluation and identification of sleep-related breathing disturbances by the analysis of the flow-volume loop of tidal breaths. This invention also relates to an apparatus for executing this method and for correcting IFL.

DESCRIPTION OF THE INVENTION

In accordance with the present invention, we found that the breath-by-breath analysis of the flow-volume loop may be helpful in identifying inspiratory flow limitation in normal sleeping subjects. Therefore, this single analysis can be used to detect the presence of upper airway obstruction. This method, besides being quite accurate, has the great advantage to not require measurements of upper airway or intrathoracic pressure. This method could easily be automated to simplify its analysis and therefore provide a simple way to determine the presence of IFL.

The analysis of the flow contour has recently been proposed to identify flow-limited breathing cycles and to determine the effective nasal continuous positive airway pressure (NCPAP) level (21). Our analysis of the airflow signal is based on the I/E flow ratio and not on the occurrence of an inspiratory flow plateauing. We developed this method because the aspect of the tracing of the inspiratory flow rate may not accurately predict IFL. In our experience, the visual interpretation of such plateauing in identifying IFL is more sensitive than our method (97.8%) because it is not influenced by modifications in the expiretory flow. However, it is much less specific (62.4%) because flow-limited breathings are characterized by a plateauing or even a decrease in the inspiratory flow rate with increasing inspiratory efforts (22), and a plateauing of the inspiratory flow can occur in the absence of flow limitation. It is probable that similar technical limitations would be observed when using an automatic analysis of the inspiratory flow tracing. Therefore, we believe that the determination of the inspiratory/expiratory flow ratio represents a practical and accurate method of identification of IFL.

With our method, flow-volume loop failed to identify IFL when the inspiratory plateau was accompanied by a greater decrease in the expiratory flow rate. This decrease in expiratory flow could be explained by the lung volume dependence of upper airway collapsibility and resistance (23,24). Recent results of our laboratory demonstrated that flow-limitation characteristics are dramatically influenced by lung deflation during continuous negative airway pressure (CNAP) manoeuvres (25). Therefore, it is possible that CNAP-induced decrease in lung volume contributed to the occurrence of false negative results by its effect on upper airway resistance. The rise in expiratory resistance contributes to the pathophysiology of sleep-related breathing disorders, as suggested by the progressive rise in inspiratory and expiratory resistance during the inter-apneic phase (26), the effects of expiratory positive airway pressure on the characteristics of apneio events (27), and by the ineffectiveness of pressure support ventilation in the treatment of SAHS (28). Since the decrease expiretory flow was responsible for most false negative analysis, we believe that our method would be even more sensitive in subjects where IFL occurs without the need to apply negative airway pressure.

Breath-by-breath analysis of flow-volume loop accurately identifies inspiratory flow limitation during CNAP manoeuvres in sleeping normal subjects. Because CNAP manoeuvres mimic the situation occurring in patients with sleep-induced air flow limitation, we therefore assume that the method fully described below is a valuable tool for evaluating sleep disorders in these patients.

This invention is herein below illustrated by the following description and figures which in no way should be limitative to the scope thereof.

FIG. 1: Example of flow-volume loops obtained during flow-limited breathing. The mid tidal volume inspiratory flow rate is less than the expiratory flow value at the same volume accounting for the decrease in the I/E ratio. With the occurrence of isolated transient changes in the EEG tracing, inspiratory flow limitation disappears with dramatic changes in the flow-volume loop and an increase in the I/E ratio. Pes: oesophageal pressure. Positive flow values correspond to inspiratory flow.

Figure 2:
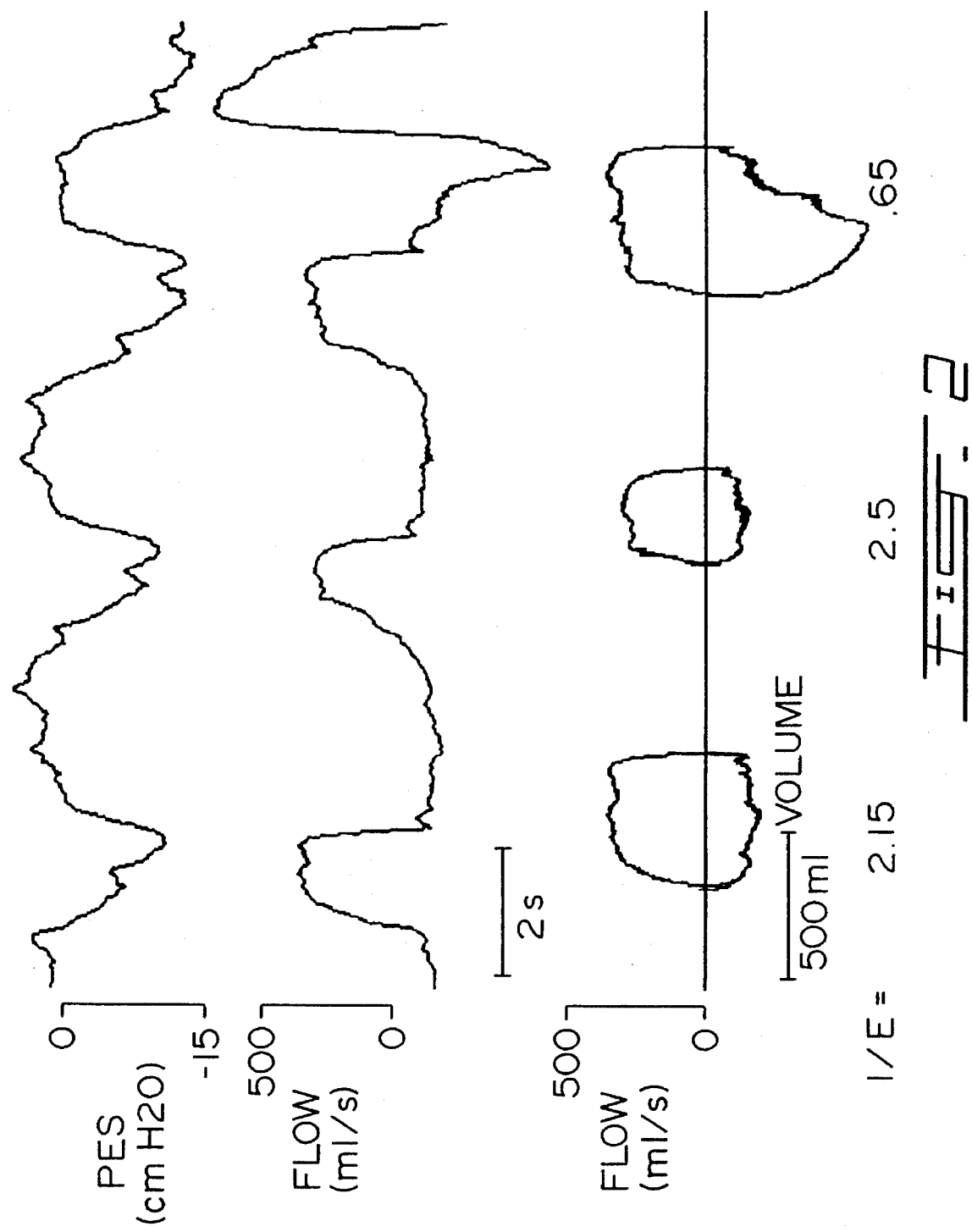

FIG. 2: Oesophageal pressure, flow, and reconstructed flow-volume loops obtained during flow-limited breathings with simultaneous plateauing of the expiratory flow. The I/E increases with the simultaneous decrease in the inspiratory and expiratory mid tidal volume flow rates. This ratio paradoxically increases with the occurrence of an arousal when the normalisation of the expiratory flow pattern precedes that of the inspiratory limb.

Figure 3:
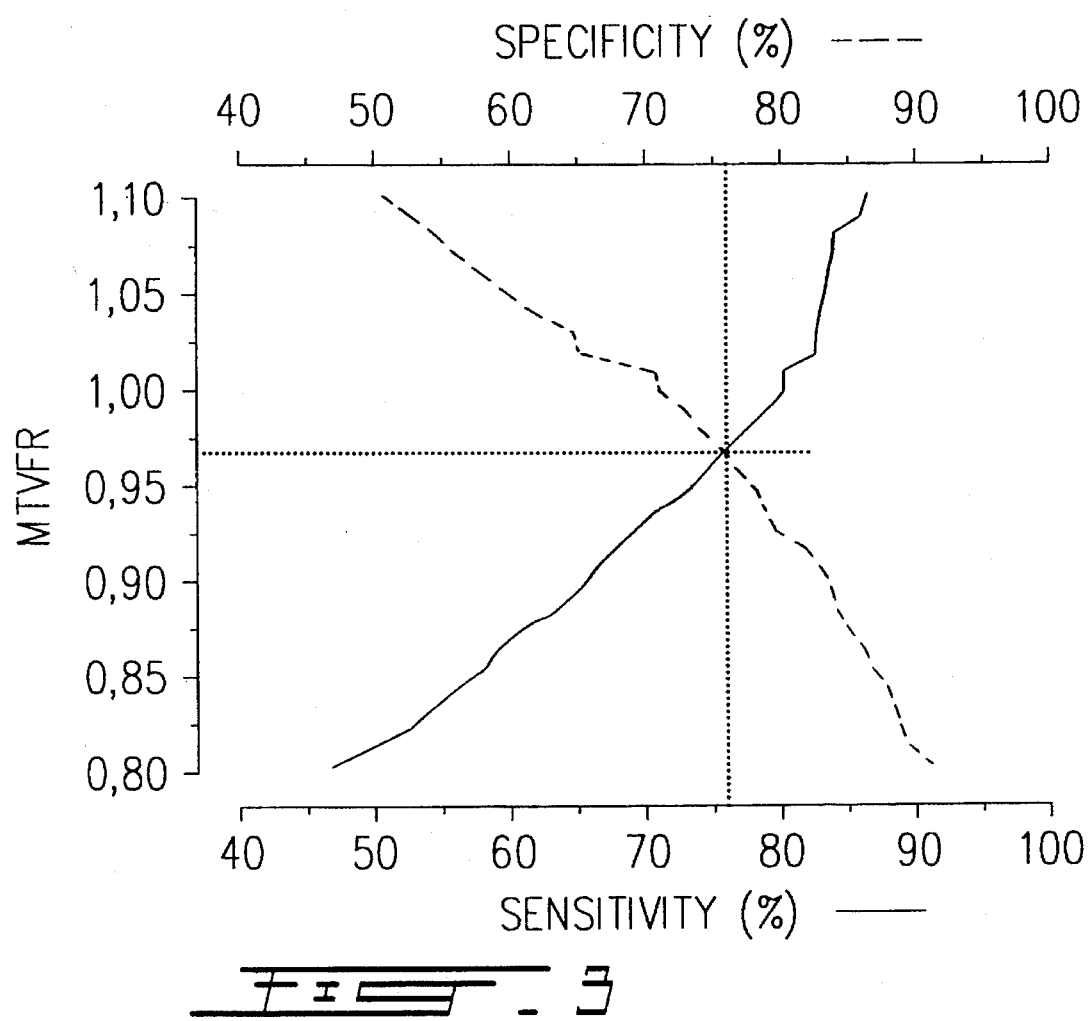

FIG. 3: Changes in the sensitivity and specificity values of the analysis of the flow-volume loop in identifying inspiratory flow-limited breathing cycles depending on the value of the I/E ratio used. Optimal values of these variables corresponded to a I/E of 0.97.

Figure 4:
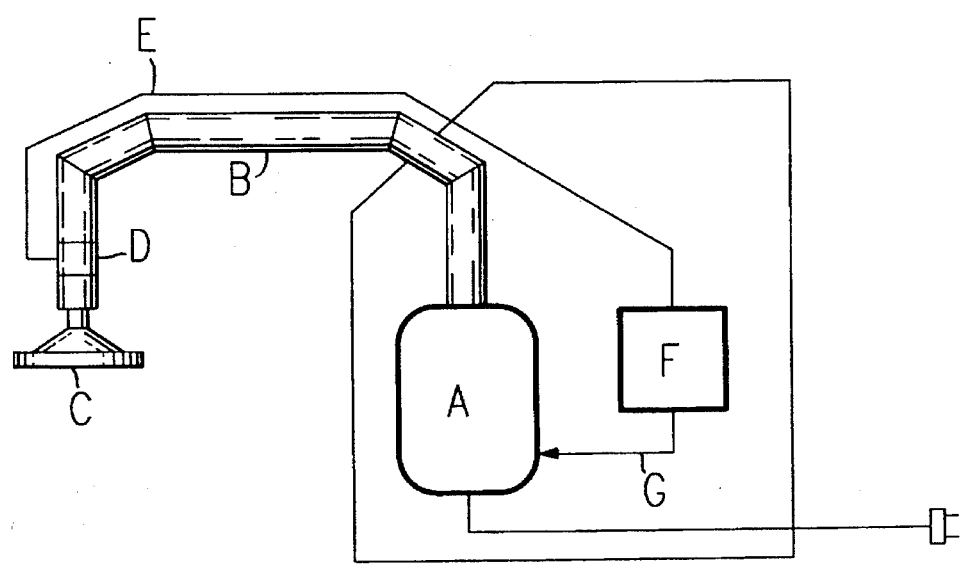

FIG. 4: Schematic representation of the CPAP apparatus according to this invention.

SUBJECTS

Seven subjects (5 males, 2 females, age range 20–27, body mass index 24.1±2.2 kg/m$^2$, means ±SD) were included in the study. All underwent a conventional polysomnographic study that confirmed their non snoring and non-apneic status- None received any medication at the time of the study. They were asked not to take alcohol for at least 24 hours before each polysomnographic study. The protocol was approved by the Ethics Review Board of our institution and a written informed consent was obtained for each subject.

UA Collapsibility

UA collapsibility was measured during continuous negative airway pressure (CNAP) trials according to the previously described technique (15). A thin wall, 5 cm latex oesophageal balloon was introduced into the nose under local anaesthesia (0.5 ml of 2% viscous lidocaine into one nostril) and positioned at about 10 cm from the cardia using the "occlusion test" procedure (20). A plastic nasal stent was placed in the anterior nostrils. All the subjects were placed in the supine position with their heads on a pre-moulded firm pillows. A tightly fitting nasal continuous positive airway pressure mask (Healthdyne, Mariette, Ga.) was applied; its airtightness was verified by occluding the openings during an inspiratory effort. One catheter was passed through one opening of the mask to measure the inside pressure (mask pressure: Pm). The mask was connected to a pneumotachograph (0.343.s$^{-1}$.mm H$_2$O, Statham type 18518 and to a T-piece. One side of the T-piece was connected to a vacuum source with a regulator. The other side was connected to a capacitance opened to ambient air with a variable orifice. A strap was placed under the chin to maintain the mouth closed and thermistor was placed over the lips to ascertain the absence of mouth breathing. Pm and oesophageal pressure (Poes) were measured using differential pressure transducers (MP-45-±100 cm H$_2$O; Validyne Corp., Northridge, Calif.) calibrated separately with a water manometer. Poes was referenced to Pm. Pm, Poes and instantaneous flow were recorded on a microcomputer; these parameters and electroencephalogram (EEG) (C$_4$/A$_1$, C$_3$/A$_2$, O$_2$/A$_1$ and O$_1$/A$_2$), electrooculogram (EOG), sub-mental electromyogram (EMG), were continuously recorded on a polygraph (78 D, Grass Instruments, Quincy, Mass.).

CNAP Protocol

Pm was maintained at approximately −1 cm H$_2$O while subjects were allowed to fall asleep. After 5–10 minutes of stage II, Pm was lowered in a step-wise fashion by −1 cm H$_2$O every 2–3 minutes. Pm was decreased until sustained arousal occurred or until an apnea was observed. One to 2 minute recording was done at each Pm level. At awakening, Pm was returned to baseline (−1 cm H$_2$O), and subjects were allowed to resume sleep before Pm was again decreased as described above. The protocol was continued until subjects were no longer able to reinitiate sleep.

Data Analysis

The breath-by-breath analysis of tidal volume was obtained by computer-integration of the instantaneous airflow signal. The flow-volume loop was reconstructed for each breathing cycle by plotting the instantaneous flow and the tidal volume (FIG. 1). The instantaneous inspiratory and expiratory flows were measured at a 50% of the respective (inspiratory or expiratory) portion of the tidal volume to obtain a breath-by-breath analysis of the mid tidal volume flow ratio (I/E ratio) (FIG. 1). We also measured the maximal inspiratory airflow ($V_{Imax}$) of each inspiratory flow-limited cycle where the flow signal became maximal and plateaued independently of the changes in Poes.

Statistical Comparisons

The conventional criteria used to determine the flow-limitation were compared to the results of the flow-volume loop analysis. The accuracy of the flow volume loop analysis was evaluated by a contingency analysis with a two-tail Fisher exact test. Since the number of recorded breathing cycles differed from one subject to another, values of the contingency analysis were balanced for the number of individual data. The relationship between the breath-by-breath values of $V_{Imax}$ and the corresponding I/E was examined by a least squares linear regression analysis.

Results

Flow-limited breathing cycles were observed for each subject during sleep. An example of the sleep recording and respiratory variables and the corresponding flow-volume loops is given in FIG. 1. The aspect of the flow-volume loop suggests an extra-thoracic obstruction with inspiratory plateauing and a normal expiratory limb. The flow pattern returned to normal with the occurrence of a K complex (FIG. 1) or an awakening; this was accompanied by dramatic changes in the aspect of the flow-volume curve that was no longer suggestive of an extra-thoracic obstruction. When this return to a normal flow pattern occurred during late inspiration, it was accompanied by a paradoxical decrease in the I/E ratio (FIGS. 1 and 2). This ratio was always greater than i during wakefulness. During sleep, it decreased in flow limited breathing cycles (FIG. 1). In 6/7 subjects there was a positive significant relationship between I/E and $V_{Imax}$ for flow-limited breathings (correlation coefficient range: 0.25–0.54).

A total of 1231 cycles were analyzed to determined the accuracy of the analysis of the flow-volume loop in identifying IFL when compared to standard IFL criteria. Since this accuracy depends on the value of I/E ratio used to define a normal flow-volume loop, this analysis was done taking a normal cutoff from 0.80 to 1.10. An I/E ratio threshold of 0.97 gave the optimal sensitivity and specificity values (both 76%, values balanced for the number of individual data, $p=10^{-4}$) (FIG. 3). Interestingly, when the diagnostic criteria that is commonly used during wakefulness to define an extra thoracic obstruction (I/E<1) was used to identify upper airway obstruction, the analysis of the flow-volume loop had a sensitivity of 80.6% and a specificity of 71.3% (FIG. 3). False negative results were due to the plateauing of the expiratory flow rate with decreases exceeding that of the inspiratory flow (FIG. 2). False negative and positive results were observed mostly at low negative mask pressures.

Since the decrease in expiratory flow was responsible for most false negative analysis, we believe that our method would be even more sensitive in subjects where IFL occurs without the need to apply negative airway pressure. We therefore assume that this method is applicable to patients suffering airflow limitation during their sleep.

The apparatus illustrated in FIG. 4 is designed for measuring and correcting the IFL by applying a Continuous Positive Airway Pressure (CPAP).

This apparatus is constructed to include the following elements:
- a nasal mask (C) which closely fits the nose of a patient and connected to a pneumotachograph (D) through connective means (tubing B);
- the pneumotachograph perceives and transmits instantaneous flow (E) signal to a computer (F) capable of integrating this signal and of measuring a I/E ratio;
- this computer retro-controls (G) a compressor (A) supplying positive air pressure through a second portion by tubing (B) and which annuls the deficit in air pressure first measured.

This device will be used to automatically modify the level of positive pressure to be applied to abolish sleep-related episodes of IFL in sleep apnea hypopnea patients. As illustrated, a pneumotachograph will be added to the circuit of a Continuous Positive Airway Pressure (CPAP) apparatus to provide the instantaneous flow signal. This signal will be automatically analyzed according to the previous described method by an integrated computer. This computer will retro-control the CPAP flow regimen according on the inspiratory/expiratory flow ratio, and the CPAP level will be modified to continuously maintain in this ratio in the non IFL range.

REFERENCES

1) Haponik EF, Smith PL, Bohlman, ME, Allen Goldman, SM, Bleecker ER. Computorized tomography in obstruction sleep apnea. Am Rev Respir Dis 1983; 127: 221–226.
2) Suratt PM, Dee P, Atkinson, RL, Armstrong, P. Wilhoit SC. Fluoroscopic and computed tomography in obstructive sleep apnea. Am Rev Respir Dis 1983; 127: 487–492.
3) Anch AM, Remmers, JE, Bunce III H. Supraglottic airway resistance in normal subjects and patients with occlusive sleep apnea. J Appl Physiol 1982; 53: 1158–1163.
4) Haponick EF, Bleecker, ER, Allen RP, Smith PL, Kaplan J. Abnormal inspiratory flow-volume curves in patients with sleep-disordered breathing. Am Rev Respir Dis 1981; 124: 571–574.
5) Sanders MH, Martin RJ, Pennock BE, Rogers RM. The detection of sleep apnea in the awake patients. JAMA 1981; 245: 2414–2418.
6) Tammelin BR, Wilson AF, De Berry Borowiecki B. Sassin JF. Flow-volume curves reflect pharyngeal airway abnormalities in sleep apnea syndrome. Am Rev Respir Dis 1983; 128: 712–715.
7) Krieger J, Weitzenblum E, Vandevenne A, Stierle JL, Kurtz D. Flow-volume curve abnormalities and obstructive sleep apnea syndrome. Chest 1985; 87: 163–167.
8) Hoffstein V, wright s, Zamel N. Flow-volume curves in snoring patients with and without obstructive sleep apnea. Am Rev Respir Dis 1989; 139: 957–960.
9) Shore ET, Millman RP. Abnormalities in the flow-volume loop in obstructive sleep apnoea sitting and supine. Thorax 1984; 39: 775–779.
10). Shepard JW, Burger CD, Nasal and oral flow-volume loops in normal subjects and patients with obstructive sleep apnea. Am Rev Respir Dis 1990; 142: 1288–1293.
11) Rodenstein DO, Stanescu DC. Soft palate and oronasal breathing in humans. J Appl Physiol 1984; 57: 651–657.
12) Kayaleh RF, Dutt, A. Khan A, Wilson AF. Tidal breath flow-volume curves in obstructive sleep apnea. Am Rev Respir Dis 1992; 145: 1372–1377.
13) Hudgel DW, Hendricks C, Hamilton HB. Characteristics of the upper airway pressure-flow relationship during sleep. J Appl Physiol 1988; 64: 1930–1935.
14) Smith PL, Wise RA, Gold AR, Schwartz AR, Permutt S. Upper airway pressure-flow relationships in obstructive sleep apnea. J Appl Physiol 1988; 64: 789–795.
15) Gleadhill IC, Schwartz AR, Schubert N, Wise RA, Permutt S, Smith PL. Upper airway collapsibility in snorers and in patients with obstructive hypopnea and apnea. Am Rev Respir Dis 1991; 143: 1300–1303.
16) Isono S, Morrison DL, Launois SH, Feroah TR, Whitelaw, WA, Remmers JE. Staic mechanics of the velopharynx of patients with obstructive sleep apnea. J Appl Physiol 1993; 75: 148–154.
17) Guilleminault C, Stoohs R, Clerk A, Cetel M, Maistros P. A cause of excessive daytime sleepiness. The upper airway resistance syndrome. Chest 1993; 104: 781–787.
18) Martin RJ, chairman. Indications and standards for cardiopulmonary sleep studies. Am. Rev. Respir. Dis. 1989; 139: 559–568.
19) Gould GA, Whyte KF, Rhind GB, Airlie MAA, Catterall JR, Shapiro CM, Douglas NJ. The sleep hypopnea syndrome. Am Rev. Respir Dis 1988; 137: 895–898.
20) Baydur, A, Berhakis PK, Zin WA, Jaeger M, Milic-Emili J. A simple method for assessing the validity of the oesophageal balloon technique. Am Rev Respir Dis 1982; 126: 788–791.
21) Condos R, Peduzzi N, Norman RN, Goldring RM, Rapoport DM. Non-invasive assessment of residual upper airway resistance during CPAP therapy of obstructive sleep apnea. Am Rev Respir Dis 1993; 147: 251.
22) Schwartz AR, Smith PL, Wise RA, Bankman I, Permutt S. Effect of positive nasal pressure on upper airway pressure-flow relationships. J Appl Physiol 1989; 66: 1626–1634.
23) Bradley TD, Brown IG, Grossman RF, Zamel N, Martinez D, Phillipson, EA and Hoffstein V. Pharyngeal size in snorers, nonsnorers, and patients obstructive sleep apnea. N Engl J Med 1986; 315: 1327–1331.
24) Series F, Cormier Y, Desmeules M. Influence of passive changes of lung volume on upper airways. J Appl Physiol 1990; 68: 2159–2164.
25) Series F, Marc I. Effects of continuous negative airway pressure-related lung deflation on upper airway collapsibility. J Appl Physiol 1993; 75: 1222–1225.
26) Sanders MH, Moore SE. Inspiratory and expiratory partitioning of airway resistance during sleep in patients with sleep apnea. Am Rev Respir Dis 1983 127: 554–558.

27) Mahadevia AK, Onal E, Lopata M. Effects of expiratory positive airway pressure on sleep induced respiratory abnormalities in patients with hypersomnia-sleep apnea syndrome. Am Rev Respir Dis 1986: 134: 555–558.

28) Sanders NH, Kern N. Obstructive sleep apnea treated by independently adjusted inspiratory and expiretory airway pressures via nasal mask. Chest 1990; 98: 317–324.

The embodiments of the invention in which an exclusive property or privilege is claimed are defined as follows:

1. A non-invasive method of detecting airflow limitation in a patient, which comprises:
   installing a tightly fitting nasal mask on the nose of said patient, said mask having an outlet port connected to one end of a tubing;
   connecting another end of said tubing to a pneumotachograph;
   obtaining an instantaneous airflow signal from said pneumotachograph when said patient is breathing;
   obtaining, by integrating calculation of said instantaneous airflow signal, the following parameters:
   a value of a breath-by-breath tidal volume;
   a flow-volume loop for each breathing cycle by plotting said instantaneous airflow signal and said breath-by-breath tidal volume;
   instantaneous inspiratory and expiratory flow values at 50% of each inspiratory and expiratory portion of said tidal volume, these values being obtained from said flow-volume loop;
   a ratio of the value of said instantaneous inspiratory flow at 50% of inspiratory portion of said tidal volume divided by the value of said instantaneous expiratory flow at 50% of expiratory portion of said tidal volume, obtaining this way a mid tidal volume flow ratio (MTVFR);
   whereby said patient having a MTVFR lower than 0.97 is diagnosed as suffering of airflow limitation.

2. The method of claim 1 further using a computer to make said integrating calculation.

3. An apparatus for detecting and correcting airflow limitation in a patient, which comprises:
   a first tubing;
   a second tubing;
   a compressor;
   a tightly fitting nasal mask adapted to be installed on the nose of said patient, said mask having an outlet port connected to one end of said first tubing;
   a pneumotachograph which has a first outlet port connected to another end of said first tubing and which has a second outlet port connected to one end of said second tubing, another end of said second tubing being connected to said compressor;
   computer means for reading and integrating an instantaneous airflow signal from said pneumotachograph, which reading and integrating result in the calculation of the following parameters:
   a breath-by-breath tidal volume;
   an instantaneous inspiratory flow value (I) and an instantaneous expiratory flow value (E) at 50% of the inspiratory and expiratory portion of said tidal volume, respectively; and
   a I/E ratio;
   said computer means sending a retro-control signal to said compressor;
   whereby airflow limitation is detected in said patient when the I/E ratio is lower than 0.97 and said airflow limitation is corrected by activating, said compressor supplying a positive air pressure to said patient through said second tubing, pneumotachograph, first tubing and nasal mask.

4. An apparatus for detecting airflow limitation in a patent, which comprises:
   a tubing;
   a tightly fitting nasal mask adapted to be installed on the nose of said patient, said mask having an outlet port connected to one end of said tubing;
   a pneumotachograph which has an outlet port connected to another end of said tubing;
   computer means for reading and integrating an instantaneous airflow signal from said pneumotachograph, which reading and integrating result in the calculation of the following parameters:
   breath-by-breath tidal volume;
   an instantaneous inspiratory flow value (I) and an expiratory flow value (E) at 50% of the inspiratory and expiratory portion of said tidal volume, respectively; and
   a I/E ratio;
   whereby airflow limitation is detected in said patient when the I/E ratio is lower than 0.97.

5. A non-invasive method of detecting and correcting airflow limitation in a patient, which comprises:
   installing a tightly fitting nasal mask on the nose of said patient, said mask having an outlet port connected to one end of a first tubing, another end of said first tubing being connected to a first outlet port of a pneumotachograph, a second outlet port of said pneumotachograph being connected to one end of a second tubing, another end of said second tubing being connected to a compressor;
   obtaining an instantaneous airflow signal from said pneumotachograph when said patient is breathing;
   obtaining by integrating calculation of said instantaneous airflow signal, the following parameters:
   value of a breath-by-breath tidal volume;
   a flow-volume loop for each breathing cycle by plotting said instantaneous airflow signal and said breath-by-breath tidal volume;
   instantaneous inspiratory and expiratory flow values at 50% of each inspiratory and expiratory portion of said tidal volume, these values being obtained from said flow-volume loop;
   a ratio of the value of said instantaneous inspiratory flow at 50% of inspiratory portion of said tidal volume divided by the value of said instantaneous expiratory flow at 50% of expiratory portion of said tidal volume, obtaining this way a mid tidal volume flow ratio (MTVFR);
   whereby said patient having a MTVFR lower than 0.97 is diagnosed as suffering of airflow limitation, and airflow is corrected by activating said compressor supplying positive air pressure to said patient through said second tubing, pneumotachograph, first tubing and nasal mask.

6. The method of claim 5 further using a computer to make said integrating calculation and to activate said compressor.

* * * * *